United States Patent
Gunderson et al.

(10) Patent No.: US 11,793,423 B2
(45) Date of Patent: Oct. 24, 2023

(54) COUGH DETECTION USING FRONTAL ACCELEROMETER

(71) Applicant: Medtronic, Inc., Minneapolis, MN (US)

(72) Inventors: Bruce D. Gunderson, Plymouth, MN (US); Gautham Rajagopal, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 157 days.

(21) Appl. No.: 17/306,372

(22) Filed: May 3, 2021

(65) Prior Publication Data

US 2022/0346667 A1 Nov. 3, 2022

(51) Int. Cl.
*A61B 5/08* (2006.01)
*A61B 5/00* (2006.01)

(52) U.S. Cl.
CPC ............ *A61B 5/0823* (2013.01); *A61B 5/686* (2013.01); *A61B 5/7207* (2013.01); *A61B 5/7246* (2013.01); *A61B 2562/0219* (2013.01)

(58) Field of Classification Search
CPC ..... A61B 5/0823; A61B 5/686; A61B 5/7207; A61B 5/7246; A61B 2562/0219; A61B 5/1122; A61B 5/0538; A61B 5/361; A61B 5/29; A61B 5/0205; A61B 5/7275; A61B 5/7282; A61B 5/72; A61B 5/782
See application file for complete search history.

(56) References Cited

U.S. PATENT DOCUMENTS

| | | | |
|---|---|---|---|
| 7,727,161 | B2 | 6/2010 | Coyle et al. |
| 8,758,262 | B2 | 6/2014 | Rhee et al. |
| 8,777,874 | B2 | 7/2014 | Zhang et al. |
| 10,750,976 | B1 | 8/2020 | McLane |
| 2006/0074334 | A1 | 4/2006 | Coyle |

(Continued)

FOREIGN PATENT DOCUMENTS

| | | |
|---|---|---|
| BR | 102014021762 A2 | 3/2016 |
| CN | 108294756 A | 7/2018 |

(Continued)

OTHER PUBLICATIONS

International Search Report and Written Opinion of International Application No. PCT/US2022/026257 dated Aug. 11, 2022, 13 pp.

(Continued)

*Primary Examiner* — Eric F Winakur
*Assistant Examiner* — Emily C Clement
(74) *Attorney, Agent, or Firm* — Shumaker & Sieffert, P.A.

(57) ABSTRACT

This disclosure is directed to techniques for recording and recognizing physiological parameter patterns associated with symptoms. A medical device system includes a medical device including an accelerometer configured to collect an accelerometer signal that indicates one or more patient movements that occur during a cough. Additionally, the medical device system includes processing circuitry configured to: determine whether the accelerometer signal satisfies a set of criteria corresponding to a cough pattern comprising a smooth increase from a baseline, then a sharp decrease, a peak within the sharp decrease, then a gradual return to the baseline; and identify a cough based on the determination that the accelerometer signal satisfies the set of criteria.

20 Claims, 10 Drawing Sheets

(56) References Cited

U.S. PATENT DOCUMENTS

| | | |
|---|---|---|
| 2008/0312547 A1 | 12/2008 | Wada |
| 2014/0046209 A1 | 2/2014 | Klap et al. |
| 2017/0095669 A1 | 4/2017 | Libbus et al. |
| 2017/0112412 A1 | 4/2017 | Garbos |
| 2017/0325717 A1 | 11/2017 | Dellimore et al. |
| 2018/0035924 A1 | 2/2018 | Gunderson et al. |
| 2019/0365263 A1 | 12/2019 | Raj et al. |
| 2020/0060604 A1* | 2/2020 | Mohammadi ........ A61B 5/6822 |
| 2020/0069281 A1 | 3/2020 | Chan et al. |
| 2020/0194106 A1 | 6/2020 | Olson et al. |
| 2020/0245873 A1 | 8/2020 | Frank et al. |
| 2021/0106253 A1 | 4/2021 | Gunderson |
| 2021/0153773 A1* | 5/2021 | Wei ...................... A61B 5/6823 |

FOREIGN PATENT DOCUMENTS

| | | |
|---|---|---|
| CN | 111166336 A | 5/2020 |
| RU | 172813 U1 | 7/2017 |
| WO | 2007052108 A2 | 5/2007 |
| WO | 2019241674 A1 | 12/2019 |

OTHER PUBLICATIONS

Georgescu, "Classification of Coughs Using the Wearable RESpeck Monitor," Mlnf Project (Part 1) Report, University of Edinburgh, 2019 (Applicant points out, in accordance with MPEP 609.04(a), that the year of publication, 2019, is sufficiently earlier than the effective U.S. filing date, so that the particular month of publication is not in issue.) 86 pp.

Paul et al., "Evaluation of a New Self-Contained, Ambulatory, Objective Cough Monitor," Cough Magazine, Sep. 27, 2006, 7 pp.

Drugman et al., "Objective Study of Sensor Relevance for Automatic Cough Detection," Journal of Latex Class Files, vol. 6, No. 1, Jan. 2007, 8 pp.

Mohammadi et al., "Automatic Discrimination Between Cough and Non-Cough Accelerometry Signal Artefacts," Biomedical Signal Processing and Control, vol. 52, Jul. 2019, pp. 394-402.

* cited by examiner

COUGH DETECTION USING FRONTAL ACCELEROMETER

TECHNICAL FIELD

The disclosure relates generally to medical device systems and, more particularly, medical device systems configured to monitor patient parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in generally evaluating patient health.

SUMMARY

In general, the disclosure is directed to devices, systems, and techniques for using a medical device to detect patient coughs based on an accelerometer signal indicative of one or more movements of the patient. The accelerometer signal may allow processing circuitry to determine when the patient coughs, and the character of that cough. In this way, the processing circuitry may track a number of instances in which the patient coughs over a period of time. If the rate in which the patient coughs changes over the period of time, or the severity of the cough is extreme, the processing circuitry may determine that the patient is experiencing one or more patient conditions such as chronic obstructive pulmonary disease (COPD), or experiencing an exacerbation of one or more patient conditions such as COPD.

For example, a medical device, e.g., an implantable medical device (IMD), may collect one or more accelerometer signals which may include components from various sources including components relating to a cough by the patient. In other words, if a patient coughs, the cough may be reflected in the accelerometer signal collected by the medical device. However, it may be the case that not all components in the accelerometer signal relate to cough(s) by the patient. As such, it may be beneficial to analyze the accelerometer signal to determine whether the accelerometer signal indicates a cough. For example, processing circuitry may analyze a section of accelerometer signal. If the accelerometer signal meets specific criteria, the processing circuitry may determine that a cough occurred at a time in which the section of the accelerometer signal is recorded by the medical device.

In some examples, coughs that may be characterized clinically as "hard" coughs may be of particular interest, e.g., because they indicate the status of a condition of the patient, such as COPD, or the health of the patient in general. In some examples, the specific criteria may be configured to identify hard coughs in the accelerometer signal.

In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. It may be beneficial to analyze the frontal component of the accelerometer signal to determine whether the accelerometer signal indicates a cough. For example, when coughing, especially when coughing hard, a patient may lean slightly forward sharply, causing the medical device to move along the frontal axis, the forward movement being reflected in the frontal component of the accelerometer signal. In response to the processing circuitry detecting forward movement in the frontal component of the accelerometer signal following a certain pattern, the processing circuitry may determine that a cough occurred.

The techniques of this disclosure may provide one or more advantages. For example, detecting one or more patient coughs based on only the frontal accelerometer signal collected by a medical device may allow accurate detection of coughs while using less computing power and fewer devices than methods employing an accelerometer signal along with measuring other patient parameters. More specifically, it may be beneficial to detect portions of the accelerometer signal which possibly indicate a cough, and subsequently analyze portions of the accelerometer signal in order to confirm that the accelerometer signal indicates a cough. Additionally, it may be beneficial to analyze the frontal component of the accelerometer system when detecting coughs using the accelerometer signal since the patient moves their chest forward along the frontal axis during a cough.

In some examples, a medical device system is configured to detect one or more coughs of a patient, the medical device system includes a medical device including an accelerometer configured to collect an accelerometer signal, wherein the accelerometer signal is indicative of one or more patient movements that occur during a cough. Additionally, the medical device system includes processing circuitry configured to determine whether the accelerometer signal satisfies a set of criteria corresponding to a cough pattern comprising a smooth increase from a baseline, then a sharp decrease, a peak within the sharp decrease, then a gradual return to the baseline; and identify a cough based on the determination that the accelerometer signal satisfies the set of criteria.

In some examples, a method includes: collecting, using an accelerometer of a medical device, an accelerometer signal, wherein the accelerometer signal is indicative of one or more patient movements that occur during a cough; determining whether the accelerometer signal satisfies a set of criteria corresponding to a cough pattern comprising a smooth increase from a baseline, then a sharp decrease, a peak within the sharp decrease, then a gradual return to the baseline; and identifying a cough based on determining that the accelerometer signal satisfies the set of criteria.

In some examples, a non-transitory computer-readable medium includes instructions for causing one or more processors to determine whether an accelerometer signal satisfies a set of criteria corresponding to a cough pattern comprising a smooth increase from a baseline, then a sharp decrease, a peak within the sharp decrease, then a gradual return to the baseline, wherein the accelerometer signal is collected by an accelerometer of a medical device, and is indicative of one or more patient movements that occur during a cough; and identify a cough based on the determination that the accelerometer signal satisfies the set of criteria.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

This disclosure describes techniques for detecting coughs of a patient in order to track one or more patient conditions. Changes in cough frequency may be a sign of a change in a patient condition. An increased coughing frequency or severity detected in a patient may indicate an exasperation in need of one or more medical conditions. For example, coughing frequency may provide an important metric for monitoring one or more patient conditions such as Chronic Obstructive Pulmonary Disease (COPD). Data collected by an implantable medical device (IMD), or one or more implantable or external devices, may be used to detect coughs and determine coughing frequency. For example, an IMD, or one or more other devices, may be configured to record an accelerometer signal which may include information that may be analyzed to detect coughs.

Figure 1:
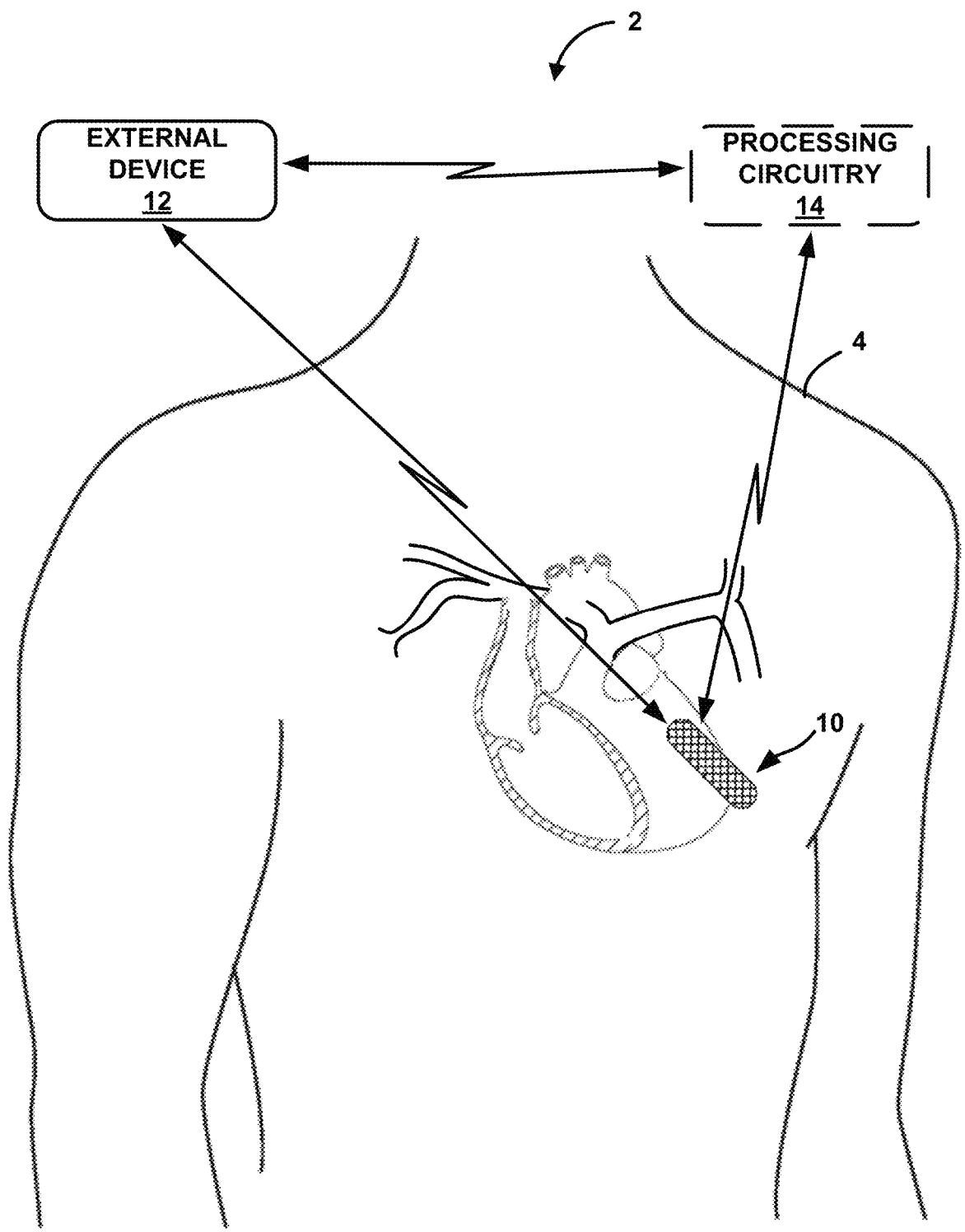
FIG. 1 illustrates the environment of an example medical device system in conjunction with a patient, in accordance with one or more techniques of this disclosure.

FIG. 1 is a conceptual diagram illustrating an environment of an example medical device system 2 in conjunction with a patient 4, in accordance with one or more techniques of this disclosure. The example techniques may be used with an IMD 10, which may be in wireless communication with at least one of external device 12 and other devices not pictured in FIG. 1. Processing circuitry 14 is conceptually illustrated in FIG. 1 as separate from IMD 10 and external device 12 but may be processing circuitry of IMD 10 and/or processing circuitry of external device 12. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10 and/or external device 12 via a network.

In some examples, IMD 10 is implanted outside of a thoracic cavity of patient 4 (e.g., subcutaneously in the pectoral location illustrated in FIG. 1). IMD 10 may be positioned near the sternum near or just below the level of patient 4's heart, e.g., at least partially within the cardiac silhouette. In some examples, IMD 10 takes the form of a LINQ™ Insertable Cardiac Monitor (ICM), available from Medtronic plc, of Dublin, Ireland.

Although in one example IMD 10 takes the form of an ICM, in other examples, IMD 10 takes the form of any combination of implantable cardiac devices (ICDs) with intravascular or extravascular leads, pacemakers, cardiac resynchronization therapy devices (CRT-Ds), neuromodulation devices, left ventricular assist devices (LVADs), implantable sensors, cardiac resynchronization therapy pacemakers (CRT-Ps), implantable pulse generators (IPGs), orthopedic devices, or drug pumps, as examples. Moreover, techniques of this disclosure may be used to measure one or more patient parameters based on signals collected by one or more of the aforementioned devices. Additionally, or alternatively, techniques of this disclosure may be used to measure one or more patient parameters based on signals collected by one or more external devices such as patch devices, wearable devices (e.g., smart watches), wearable sensors, or any combination thereof.

Clinicians sometimes diagnose patients with medical conditions based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patent is in a clinic for a medical appointment. However, in some examples, physiological markers (e.g., coughs, hard coughs, irregular heartbeats, and long-term respiration trends) of a patient condition occur when the patient is outside the clinic. As such, in these examples, a clinician may be unable to observe the physiological markers needed to diagnose a patient with a medical condition. Additionally, it may be beneficial to monitor one or more patient parameters for an extended period of time (e.g., days, weeks, or months) so that a frequency of occurrence over time of a symptom may be determined and tracked. In the example illustrated in FIG. 1, IMD 10 is implanted within patient 4 to continuously record one or more physiological signals of patient 4 over an extended period of time.

In some examples, IMD 10 includes one or more accelerometers. An accelerometer of IMD 10 may collect an accelerometer signal which reflects a measurement of a motion of patient 4. In some cases, the accelerometer may collect a three-axis accelerometer signal indicative of patient 4's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 4 along a vertical axis, the lateral axis accelerometer signal vector may represent an acceleration of patient 4 along a lateral axis, and the frontal axis accelerometer signal vector may represent an acceleration of patient 4 along a frontal axis. In some cases, the vertical axis substantially extends along a torso of patient 4 from a neck of patient 4 to a waist of patient 4, the lateral axis extends across a chest of patient 4 perpendicular to the vertical axis, and the frontal axis extends outward from and through the chest of patient 4, the frontal axis being perpendicular to the vertical axis and the lateral axis. IMD 10 may track accelerometer measurements over a period of time (e.g., hours, days, weeks, or months) and the processing circuitry may identify a trend of accelerometer values using data from the accelerometer measurements. Based on the identified trend, the processing circuitry may, in some cases, identify a medical condition present in the patient or monitor a condition that is already known to be present in the patient.

External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, include a programmer, an external monitor, or a consumer device such as a smart phone or tablet.

In other examples, external device 12 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 12 is configured for use by the clinician, external device 12 may be used to transmit instructions to IMD 10. Example instructions may include requests to set electrode combinations for sensing and any other information that may be useful for programming into IMD 10. The clinician may also configure and store operational parameters for IMD 10 within IMD 10 with the aid of external device 12. In some examples, external device 12 assists the clinician in the configuration of IMD 10 by providing a system for identifying potentially beneficial operational parameter values.

Whether external device 12 is configured for clinician or patient use, external device 12 is configured to communicate with IMD 10 and, optionally, another computing device (not illustrated by FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies). In some examples, external device 12 is configured to communicate with a computer network, such as the Medtronic CareLink® Network developed by Medtronic, plc, of Dublin, Ireland. For example, external device 12 may send data, such as data received from IMD 10, to another external device such as a smartphone, a tablet, or a desktop computer, and the other external device may in turn send the data to the computer network. In other examples, external device 12 may directly communicate with the computer network without an intermediary device.

Processing circuitry 14, in some examples, may include one or more processors that are configured to implement functionality and/or process instructions for execution within IMD 10, external device 12, one or more other devices, or any combination thereof. For example, processing circuitry 14 may be capable of processing instructions stored in a memory. Processing circuitry 14 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 14 may include any suitable structure, whether in hardware, software, firmware, or any combination thereof, to perform the functions ascribed herein to processing circuitry 14. Processing circuitry 14 may contain signal analysis circuitry which may perform signal processing techniques to extract information indicating the one or more parameters of an accelerometer signal.

Processing circuitry 14 may represent processing circuitry located within any combination of IMD 10 and external device 12. In some examples, processing circuitry 14 may be entirely located within a housing of IMD 10. In other examples, processing circuitry 14 may be entirely located within a housing of external device 12. In other examples, processing circuitry 14 may be located within any combination of IMD 10, external device 12, and another device or group of devices that are not illustrated in FIG. 1. As such, techniques and capabilities attributed herein to processing circuitry 14 may be attributed to any combination of IMD 10, external device 12, and other devices that are not illustrated in FIG. 1, e.g., one or more servers or computing devices as illustrated with respect to FIG. 6.

Processing circuitry 14 may analyze an accelerometer signal to determine whether a patient coughed, e.g., experienced a cough. Processing circuitry 14 may determine whether one or more parameter values associated with a segment of an accelerometer signal satisfy one or more criteria, e.g., is greater than a threshold parameter value. It may be beneficial for processing circuitry 14 to analyze the frontal component of the accelerometer signal in order to determine whether the patient coughed during the period of time in which the segment of the accelerometer signal is being collected. During a cough, the chest of patient 4 may move forwards along the frontal axis. In this way, the chest movement which occurs due to a cough may be recorded in the frontal component of the accelerometer signal. In some examples, the parameter value of the segment of the accelerometer signal may correspond to a magnitude value of the frontal component of the accelerometer signal. Additionally, or alternatively, in some examples, the parameter value may represent one or more of a derivative of the frontal component of the segment of the accelerometer signal, an area under the frontal component of the accelerometer signal, or another parameter corresponding to the frontal component, the vertical component, or the lateral component of the accelerometer signal.

A memory (not illustrated in FIG. 1) may be configured to store information within medical device system 2 during operation. The memory may include a computer-readable storage medium or computer-readable storage device. In some examples, the memory includes one or both of a short-term memory or a long-term memory. The memory may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, the memory is used to store program instructions for execution by processing circuitry 14.

The memory may represent a memory located within any one or both of IMD 10 and external device 12. In some examples, the memory may be entirely located within a housing of IMD 10. In other examples, the memory may be entirely located within a housing of external device 12. In other examples, the memory may be located within any combination of IMD 10, external device 12, and another device or group of devices that are not illustrated in FIG. 1. As such, techniques and capabilities attributed herein to the memory may be attributed to any combination of IMD 10, external device 12, and other devices that are not illustrated in FIG. 1.

In some examples, one or more sensors (e.g., electrodes, motion sensors (e.g., accelerometers), optical sensors, temperature sensors, or any combination thereof) of IMD 10 may sense one or more signals that indicate a parameter or set of parameters of a patient. In some examples, the signal that indicates the parameter includes a plurality of parameter values, where each parameter value of the plurality of parameter values represents a measurement, e.g., periodic measurement, of the parameter at a respective interval of time. The plurality of parameter values may represent a sequence of parameter values, where each parameter value of the sequence of parameter values are collected by IMD 10 at a start of each time interval of a sequence of time intervals. For example, IMD 10 may perform a parameter measurement in order to determine a parameter value of the sequence of parameter values according to a recurring time interval (e.g., every day, every night, every other day, every twelve hours, every hour, or any other recurring time interval). In another example, IMD 10 may perform a parameter measurement in response to a patient notification that measurement should begin. In another example, IMD 10 may constantly perform parameter measurements. In this way, IMD 10 may be configured to track a respective patient parameter more effectively as a patient need not be in a clinic for a parameter to be tracked, since IMD 10 is implanted within patient 4 and is configured to perform parameter measurements according to recurring or other time intervals without missing a time interval.

Processing circuitry 14 may receive a portion of the accelerometer signal that includes the plurality of parameter values. In this way, processing circuitry 14 may receive at least a portion of the sequence of parameter values such that processing circuitry 14 can analyze the signal in order to determine whether a signal segment of an accelerometer is indicative of a cough, e.g., a hard cough. In some examples, IMD 10 may continuously collect the accelerometer signal and/or parameter values determined from the accelerometer signal at a predetermined frequency. IMD 10, a server, or another storage device may include a buffer or other memory structure which temporarily or permanently stores the signal and/or parameter values. Processing circuitry 14 may maintain a cough database which stores a plurality of sets of data in logs corresponding to coughs of a patient. In some cases, processing circuitry 14 may remove one or more sets of data from the cough database.

Each set of data stored by the cough database may include one or more portions of signals measured by IMD 10, other implantable devices, other external devices, or any combination thereof. For example, IMD 10 may collect one or more of the accelerometer signal of an accelerometer attached to IMD 10, an accelerometer signal of an accelerometer attached to other implantable devices, an accelerometer signal of an accelerometer attached to an external device, e.g., a wearable patch device, or any combination thereof. When IMD 10 collects a signal, IMD 10 may collect a sequence of samples corresponding to the respective signal, and the sequence of samples may represent the signal itself. Consequently, a "portion" of the signal may represent set of consecutive samples of the signal. Each set of data stored by the cough database may include a portion of each signal of a set of signals, where each respective portion corresponds to a respective window of time. In some examples, the window of time corresponds to a time in which processing circuitry 14 has received data indicative of a user cough. In some examples, the window of time corresponds to a time in which processing circuitry 14 detects accelerometer signal parameters that satisfy criteria corresponding to a cough.

Processing circuitry may update the cough database when prompted. For example, processing circuitry 14 may receive data indicative of a cough, collect a set of data during the time in which the cough is being experienced, and add the set of data to the plurality of sets of data stored in the cough database along with other data such as date and time stamps, and increment a cough counter in memory.

Processing circuitry 14 may also update the symptom database on a rolling basis. For example, processing circuitry 14 may add a set of data to the plurality of sets of data stored in the cough database when processing circuitry 14 detects physiological parameters that correspond to a cough.

Processing circuitry 14 may be configured to identify coughs based on detected physiological parameter data (e.g. accelerometer signal data). Parameter values corresponding to physiological parameters may be stored in a buffer and be analyzed by an algorithm executed on processing circuitry 14. When the algorithm determines that detected physiological parameters correspond to a cough, processing circuitry 14 may alert a physician that a cough is being experienced and save the detected physiological parameters to the cough database.

Processing circuitry 14 may set one or more time windows based on the times or the periods of time in which an accelerometer signal satisfies a criterion or set of criteria corresponding to a cough pattern. For example, processing circuitry 14 may set the time window to begin at a first time and end at a second time, with the first and second times being identified relate to the time or period of time in which detected accelerometer signals are determined by an algorithm to satisfy a criterion or set of criteria corresponding to a cough. In some examples, the first time may represent a time slightly before a first criterion corresponding to a cough is detected in the accelerometer signal. In some examples, the first time is a predetermined amount of time before the time or period of time in which the first criterion corresponding to a cough is detected in the accelerometer signal. In some examples, the second time is a predetermined amount of time after the time or period of time in which the first criterion corresponding to a cough is detected in the accelerometer signal, where the second time is after the first time. In some examples, the second time may represent a time slightly after a last criterion corresponding to a cough is detected in the accelerometer signal, where the second time is after the first time. In any case, the time window may include at least a portion of time following the time in which the first feature of a cough is detected.

In some cases, processing circuitry 14 may save, to the cough database stored in a memory, a set of data including one or more accelerometer signals corresponding to the time associated with criteria corresponding to a cough detection as described above. The set of data may include a set of signal portions. Each signal portion of the set of signal portions corresponds to a respective signal collected by IMD 10 or another device and each signal portion of the set of signal portions includes data corresponding to the window of time selected by processing circuitry 14 based on the time or period of time in which signal data satisfying criteria corresponding to cough have been detected. For example, the set of data may include a portion of the accelerometer signal collected by IMD 10 from the first time to the second time, and a portion of the accelerometer signal from the first time to the second time as modified by an algorithm.

The accelerometer signal recorded by IMD 10 may include a first sequence of accelerometer signal samples. For example, IMD 10 may collect accelerometer signal samples at a predetermined or remotely configurable sampling rate in order to collect the first sequence of accelerometer signal samples. Additionally, processing circuitry 14 may be configured to generate a second sequence of accelerometer signal samples, where the second sequence of accelerometer signal samples represents a derivative of the first sequence of accelerometer signal samples. In this way, processing circuitry 14 may be configured to calculate the derivative of the accelerometer signal. Additionally, processing circuitry 14 may be configured to generate a third sequence of accelerometer signal samples, where the third sequence of accelerometer signal samples represents a long-term average of the first sequence of accelerometer signal samples. In this way, processing circuitry 14 may be configured to calculate the long-term average of the accelerometer signal. Additionally, processing circuitry 14 may be configured to generate a fourth sequence of accelerometer signal samples, where the fourth sequence of accelerometer signal samples represents a first difference of the first, second, or third sequence of accelerometer signal samples. In this way, processing circuitry 14 may be configured to calculate the first difference of the accelerometer signal. In some examples, it may be easier for processing circuitry 14 to detect features of a cough event in the derivative, long-term average, or first-difference signal. Although some examples below specify using either the accelerometer signal, the derivative signal, the long-term average signal, or the first difference signal, features indicative of a cough may be checked for in any one or more of these different signal types. Processing circuitry 14 may be configured to identify portions of the accelerometer signal which indicate different features of a cough of patient 4.

For example, an accelerometer signal may be sampled at 100 hertz (Hz). A long-term average signal may be generated from the frontal accelerometer signal by, for each sample value, computing the median of a number of previous samples (e.g., 30 samples), and compiling all the median values into a long-term average signal. For further example, a first-difference signal may be generated from the long-term average signal by calculating the value difference between each sample and another sample a number of samples following each sample (e.g. the difference between each successive sample value), and compiling all the difference values into a first-difference signal.

The accelerometer signal recorded by IMD 10 may have one or more features indicative of a cough, e.g. hard cough. In order to detect these features, an algorithm may be executed on processing circuitry 14 that analyses the accelerometer signal. The algorithm may determine that a cough event occurs when all of a number of features are present in the accelerometer signal. In order to conserve computational power, especially for internal devices with a limited power source, the algorithm may check for features step-by-step, and upon failing to identify a feature that must be present in order for the algorithm to determine that a cough event has occurred, terminate further analysis by the algorithm of that particular accelerometer signal segment, and start analysis of the next accelerometer signal segment. The algorithm may also terminate further analysis of a particular accelerometer signal segment if one of a plurality of steps executed in order to identify features of a cough event fails.

The accelerometer signal may be saved in a buffer to be analyzed. The buffer may include a number of signal samples sufficient to detect all the features required to identify a cough. An algorithm executed on processing circuitry 14 may analyze a segment of the accelerometer signal in the buffer where the segment starts on the first sample in the buffer and ends on a sample a predetermined number of samples after the first sample. If the algorithm does not identify a first feature necessary for classifying the segment of the accelerometer signal as indicative of a cough event, the algorithm may end analysis of that signal segment and start analysis of a next accelerometer signal segment. In some examples, the next accelerometer signal segment may be incremented from the first segment by one sample, or a predetermined number of samples.

The one or more features of a cough event that the algorithm executed on processing circuitry 14 may attempt to identify in a segment of the accelerometer signal may include a short period of gradual increase in the frontal accelerometer signal from a baseline, a subsequent sharp decrease in the frontal accelerometer signal, a peak in the accelerometer signal within the sharp decrease, and followed by a gradual return in the accelerometer signal to a baseline. The algorithm may also check the segment of the accelerometer signal for excessive noise, and determine that the presence of noise above a threshold level indicates faulty signal readings rather than a hard cough. The algorithm may attempt to identify these features in an order, and if one of the features is not identified, terminate analysis of that segment of the accelerometer signal.

Analyzing the features of the segment of the accelerometer signal may involve identifying one or more sub-features or performing one or more steps of a calculation. For example, processing circuitry 14 executing the algorithm may generate a long-term average signal from the segment of the accelerometer signal currently being analyzed. Within the long-term average signal, processing circuitry 14 may identify a drop-off point, a valley point, and a stabilization point. Failing to identify one of these features may cause processing circuitry 14 to terminate analysis of the accelerometer signal segment. In addition, processing circuitry 14 may determine if a ratio of a number of samples between the stabilization point and valley point to the sampling rate is both above a threshold value and below a threshold value. In addition, processing circuitry 14 may calculate an amplitude difference between the dropoff point and the valley point, and an amplitude difference between the stabilization point and the valley point. If one of the amplitude differences exceeds an upper threshold or fails to exceed a lower threshold, Processing circuitry 14 may terminate analysis of the accelerometer signal segment. Processing circuitry 14 may identify other features within the accelerometer signal segment, including noisy fluctuations in a portion of the accelerometer signal segment before the dropoff point. Processing circuitry 14 may also identify a peak point between the dropoff point and the valley point. Further description of these features may be found below in FIGS. 7-9.

Processing circuitry 14 may increment, in response to determining that all features necessary for classifying a frontal accelerometer signal as indicative of a cough event, a cough count value. In some examples, processing circuitry 14 may attach a time stamp to the detected cough so that processing circuitry 14 may determine a time in which each detected cough occurs. In some cases, processing circuitry 14 is configured to determine, based on the cough count value, a cough rate associated with the patient, where the cough rate represents a number of coughs detected per unit time. Processing circuitry 14 may be configured to track the cough rate associated with patient 4 over a period of time. In this way, processing circuitry 14 may identify one or more trends in the cough rate over the period of time. In some cases, if the cough rate increases from a first point in time to a second point in time, processing circuitry 14 may determine, that a patient condition (e.g., COPD) is occurring and/or worsening. In some examples, processing circuitry 14 is further configured to output an alert indicting the occurrence and/or the worsening of the patient condition identified by processing circuitry 14.

In some examples, to identify the one or more trends in the cough rate, processing circuitry 14 may perform a statistical process control (SPC) based on cough rate data over a period of time. For example, cough rate data may include a set of cough rate values that are collected over the period of time. Processing circuitry 14 may determine a baseline cough rate value based on the set of cough rate values. If a cough rate value of the set of cough rate values is greater than the baseline cough rate value by more than a threshold cough rate difference value, processing circuitry 14 may determine that a worsening of one or more patient conditions (e.g., COPD) occurs at a time in which the cough rate value is measured.

In some examples, it may be beneficial to detect coughing exacerbations in order to manage one or more patient conditions, such as COPD. For example, it may be beneficial to track a coughing frequency of patient 4 over a period of time lasting days or weeks. Processing circuitry 14 may detect acute exacerbation in coughing, allowing patient 4 to receive treatment for such a condition. Coughing exacerbations may be caused by a respiratory infection, air pollution, or other triggers of lung inflammation.

Figure 2:
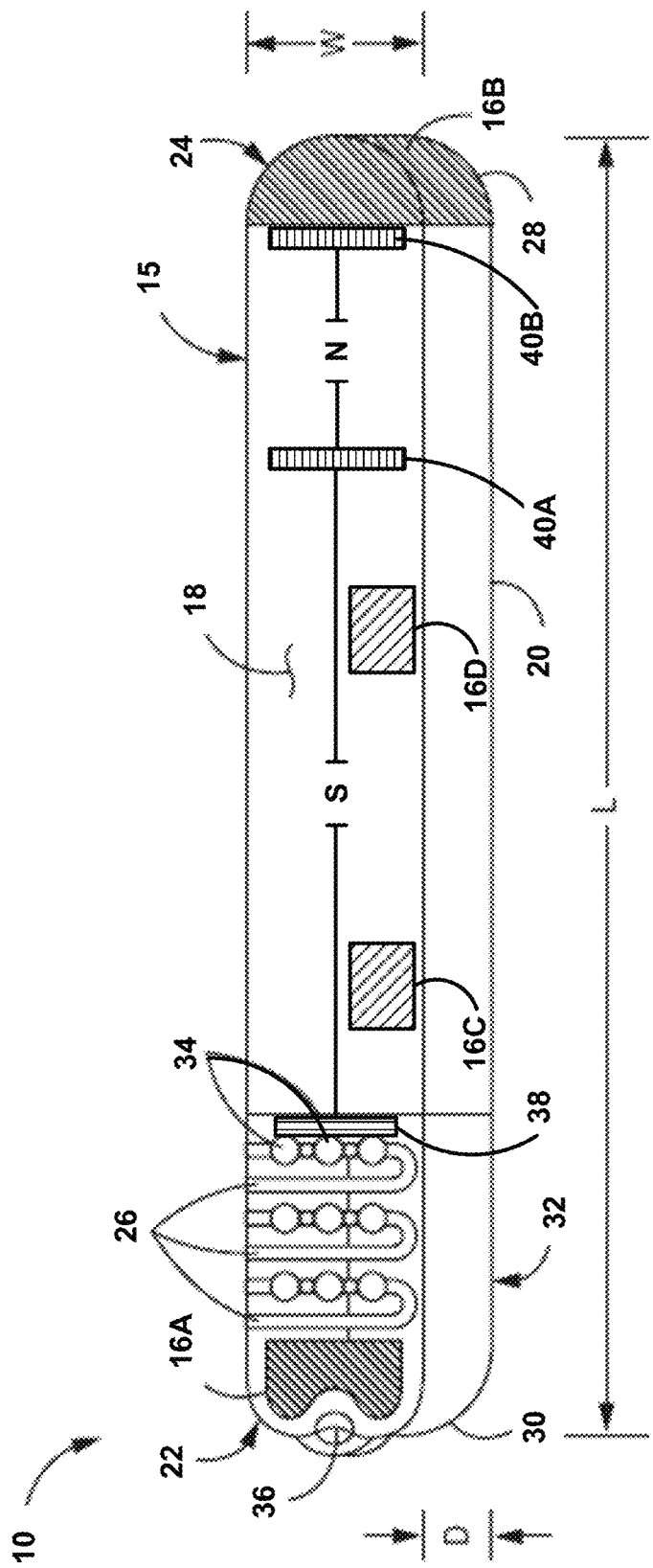
FIG. 2 is a conceptual drawing illustrating an example configuration of the implantable medical device (IMD) of the medical device system of FIG. 1, in accordance with one or more techniques described herein.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 16A, and distal electrode 16B. Housing 15 may further include first major surface 18, second major surface 20, proximal end 22, and distal end 24. In some examples, IMD 10 may include one or more additional electrodes 16C, 16D positioned on one or both of major surfaces 18, 20 of IMD 10. Housing 15 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 15. In some examples, electrode 16B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 16A and distal electrode 16B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of first major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4.

In the example shown in FIG. 2, first major surface 18 of IMD 10 faces outward towards the skin, when IMD 10 is inserted within patient 4, whereas second major surface 20 faces inward toward musculature of patient 4. Thus, first and second major surfaces 18, 20 may face in directions along a sagittal axis of patient 4 (see FIG. 1), and this orientation may be maintained upon implantation due to the dimensions of IMD 10.

Proximal electrode 16A and distal electrode 16B may be used to sense cardiac EGMs (e.g., cardiac ECGs) when IMD 10 is implanted subcutaneously in patient 4. In some examples, processing circuitry of IMD 10 also may determine whether cardiac EGMs of patient 4 are indicative of arrhythmia or other abnormalities (e.g., heart failure, sleep apnea, or COPD), which processing circuitry of IMD 10 may evaluate in determining whether a medical condition of patient 4 has changed. The cardiac EGMs may be stored in a memory of the IMD 10. In some examples, data derived from the EGMs may be transmitted via integrated antenna 26 to another medical device, such as external device 12. In some examples, one or both of electrodes 16A and 16B also may be used by IMD 10 to collect one or more impedance signals (e.g., a subcutaneous tissue impedance) during impedance measurements performed by IMD 10. In some examples, such impedance values detected by IMD 10 may reflect a resistance value associated with a contact between electrodes 16A, 16B, and target tissue of patient 4. Additionally, in some examples, electrodes 16A, 16B may be used by communication circuitry of IMD 10 for tissue conductance communication (TCC) communication with external device 12 or another device.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, Wi-Fi®, or other proprietary or non-proprietary wireless telemetry communication schemes. Antenna 26 may be coupled to communication circuitry of IMD 10, which may drive antenna 26 to transmit signals to external device 12 and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 15 may include anti-migration projections 34 positioned adjacent integrated antenna 26. Anti-migration projections 34 may include a plurality of bumps or protrusions extending away from first major surface 18 and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may include a molded header assembly made from a polymeric or plastic material, which may be integrated or separable from the main portion of IMD 10.

Electrodes 16A and 16B may be used to sense cardiac EGMs, as described above. Additional electrodes 16C and 16D may be used to sense subcutaneous tissue impedance, in addition to or instead of electrodes 16A, 16B, in some examples. In some examples, processing circuitry of IMD 10 may determine an impedance value of patient 4 based on signals received from at least two of electrodes 16A-16D. For example, processing circuitry of IMD 10 may generate one of a current or voltage signal, deliver the signal via a selected two or more of electrodes 16A-16D, and measure the resulting other of current or voltage. Processing circuitry of IMD 10 may determine an impedance value based on the delivered current or voltage and the measured voltage or current.

In the example shown in FIG. 2, IMD 10 includes light emitter(s) 38 and a proximal light detector 40A and a distal light detector 40B (collectively, "light detectors 40") positioned on housing 15 of IMD 10. Light detector 40A may be positioned at a distance S from light emitter(s) 38, and a distal light detector 40B positioned at a distance S+N from light emitter(s) 38. In other examples, IMD 10 may include only one of light detectors 40A, 40B, or may include additional light emitters and/or additional light detectors. Collectively, light emitter(s) 38 and light detectors 40A, 40B may include an optical sensor, which may be used to determine $StO_2$ or $SpO_2$ values of patient 4. Although light emitter(s) 38 and light detectors 40A, 40B are described herein as being positioned on housing 15 of IMD 10, in other examples, one or more of light emitter(s) 38 and light detectors 40A, 40B may be positioned, on a housing of another type of IMD within patient 4, such as a transvenous, subcutaneous, or extravascular pacemaker or ICD, or connected to such a device via a lead.

IMD includes one or more accelerometers (not illustrated in FIG. 2). Such accelerometers may be 3D accelerometers configured to generate signals indicative of one or more types of movement of the patient, such as gross body movement (e.g., motion) of the patient, patient posture, movements associated with the beating of the heart, coughing, or hard coughing, rales, or other respiration abnormalities. One or more of the parameters monitored by IMD 10 (e.g., impedance, EGM) may fluctuate in response to changes in one or more such types of movement. For example, changes in parameter values sometimes may be attributable to increased patient motion (e.g., exercise or other physical motion as compared to immobility) or to changes in patient posture, and not necessarily to changes in a medical condition. Thus, in some methods of identifying or tracking a medical condition of patient 4, it may be advantageous to account for such fluctuations when determining whether a change in a parameter is indicative of a change in a medical condition.

Figure 3:
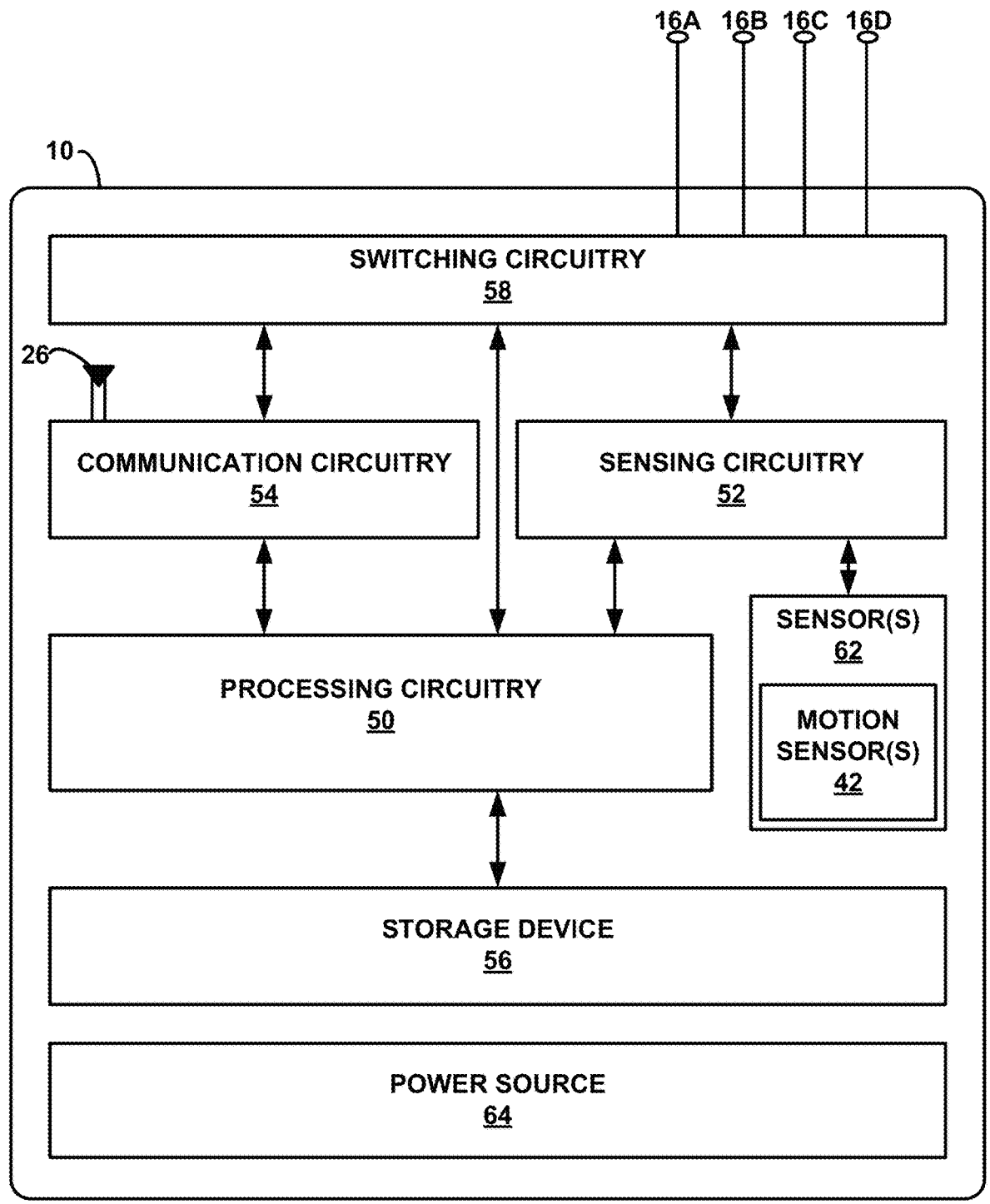
FIG. 3 is a functional block diagram illustrating an example configuration of the IMD of FIGS. 1 and 2, in accordance with one or more techniques described herein.

FIG. 3 is a functional block diagram illustrating an example configuration of IMD 10 of FIGS. 1 and 2, in accordance with one or more techniques described herein. As seen in FIG. 3, IMD 10 includes electrodes 16A-16D (collectively, "electrodes 16"), antenna 26, processing circuitry 50, sensing circuitry 52, communication circuitry 54, storage device 56, switching circuitry 58, sensors 62 including motion sensor(s) 42, and power source 64.

Motion sensor(s) 42 may include one or more accelerometers capable of tracking motion in one or more axes. For example, in some examples, motion sensor(s) 42 may include a vertical axis accelerometer, a lateral axis accelerometer, and a frontal axis accelerometer. In some examples, motion sensor(s) 42 may include a multi-axis accelerometer capable of tracking vertical, lateral, and frontal axis motion. Motion sensor(s) 42 may be positioned in any known configuration in or on IMD 10.

Processing circuitry 50 may include fixed function circuitry and/or programmable processing circuitry. Processing circuitry 50 may include, for example, microprocessors, DSPs, ASICs, FPGAs, equivalent discrete or integrated logic circuitry, or a combination of any of the foregoing devices or circuitry. Accordingly, processing circuitry 50 may include any suitable structure, whether in hardware, software, firmware, or any combination thereof, to perform the functions ascribed herein to IMD 10. In some examples, processing circuitry 50 may represent at least a portion of processing circuitry 14 of FIG. 1, but this is not required. In some examples, processing circuitry 50 may be separate from processing circuitry 14 of FIG. 1.

Sensing circuitry 52 and communication circuitry 54 may be selectively coupled to electrodes 16 via switching circuitry 58, which may be controlled by processing circuitry 50. Sensing circuitry 52 may monitor signals from electrodes 16 in order to monitor electrical activity of heart (e.g., to produce an EGM), and/or subcutaneous tissue impedance, the impedance being indicative of at least some aspects of patient 4's cardiac activity and/or respiratory patterns. Sensing circuitry 52 also may monitor signals from sensors 62, which may include light detectors 40, motion sensor(s) 42, and any additional sensors that may be positioned on IMD 10. In some examples, sensing circuitry 52 may include one or more filters and amplifiers for filtering and amplifying signals received from one or more of electrodes 16 and/or sensor(s) 62. In some examples, sensing circuitry 52 may contain an analog to digital converter (ADC) for digitizing sensor signals.

Communication circuitry 54 may include any suitable hardware, firmware, software or any combination thereof for communicating with another device, such as external device 12 or another device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include one or both of a short-term memory or a long-term memory. The memory may include, for example, RAM, DRAM, SRAM, magnetic discs, optical discs, flash memories, or forms of EPROM or EEPROM. In some examples, the memory is used to store program instructions for execution by processing circuitry 50.

Power source 64 is configured to deliver operating power to the components of IMD 10. Power source 64 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 64 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 4A:
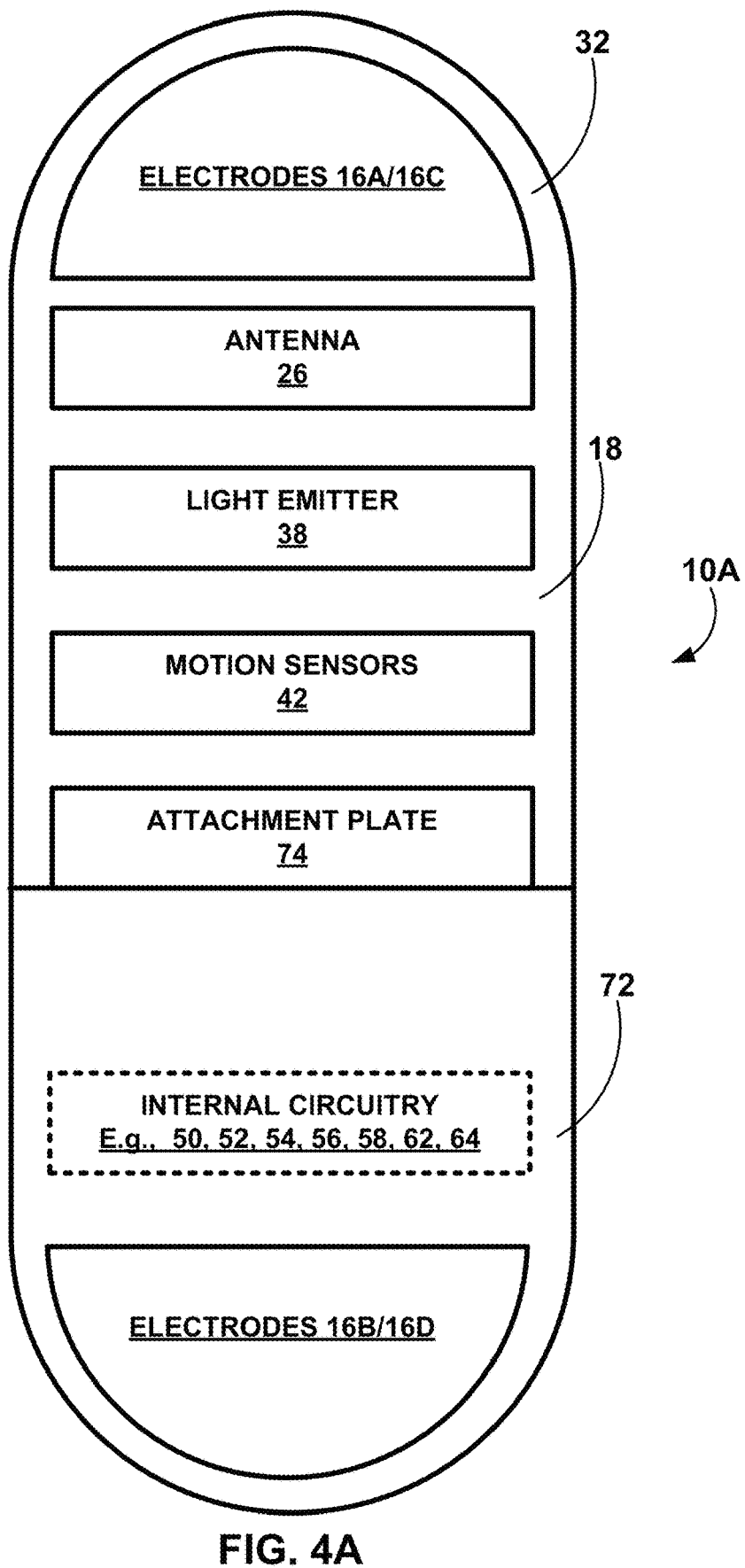
FIGS. 4A and 4B illustrate two additional example IMDs that may be substantially similar to the IMD of FIGS. 1-3, but which may include one or more additional features, in accordance with one or more techniques described herein.
Figure 4B:
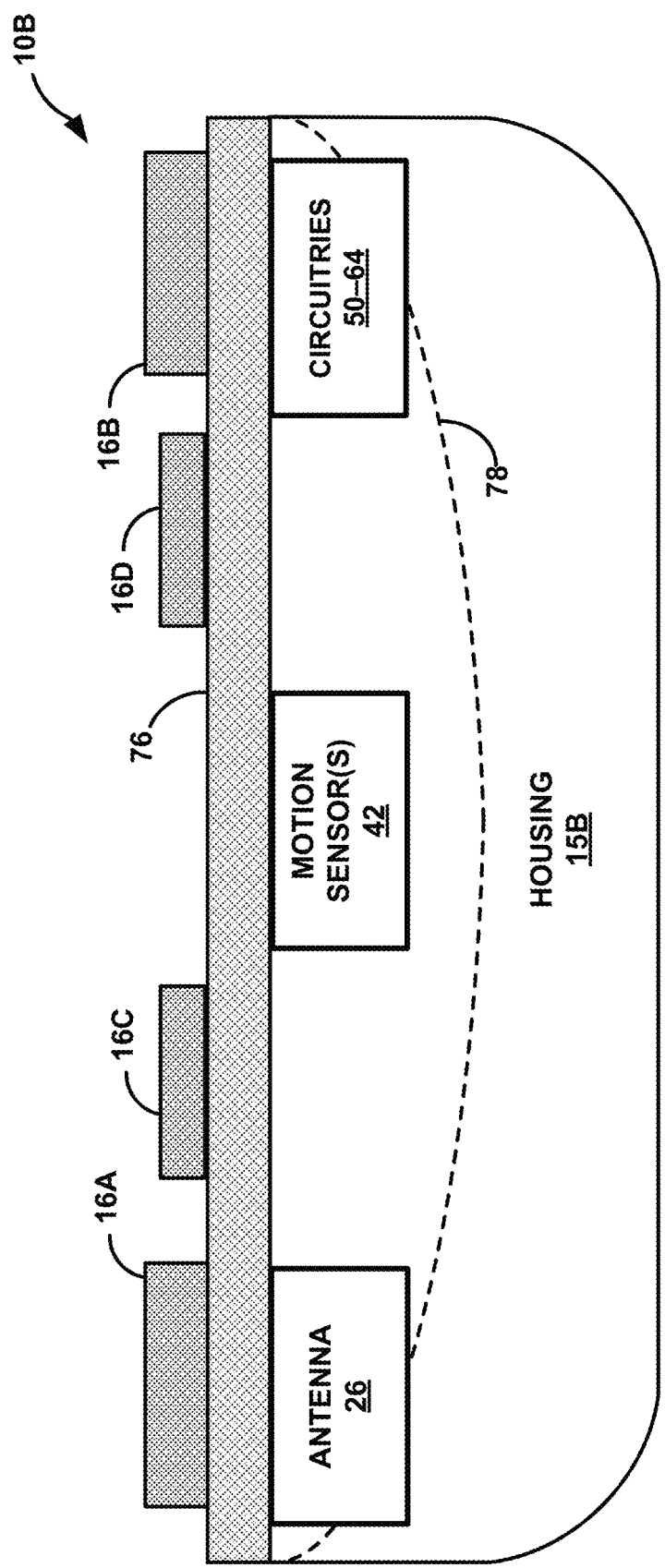

FIGS. 4A and 4B illustrate two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, storage device 56, switching circuitry 58, internal components of sensors 62, and power source 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and/or light detectors 40A, 40B on housing 15B and processing circuitry 50. In some examples, insulative cover 76 may be positioned over an open housing 15 to form the housing for the components of IMD 10B. One or more components of IMD 10B (e.g., antenna 26, light emitter 38, motion sensors 42, processing circuitry 50, sensing circuitry 52, communication circuitry 54, switching circuitry 58, and/or power source 64) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Insulative cover 76 may be configured so as not to interfere with the operation of IMD 10B. For example, one or more of electrodes 16A-16D may be formed or placed above or on top of insulative cover 76, and electrically connected to switching circuitry 58 through one or more vias (not shown) formed through insulative cover 76. Insulative cover 76 may be formed of sapphire (i.e., corundum), glass, parylene, and/or any other suitable insulating material. Sapphire may be greater than 80% transmissive for wavelengths in the range of about 300 nm to about 4000 nm, and may have a relatively flat profile. In the case of variation, different transmissions at different wavelengths may be compensated for, such as by using a ratiometric approach. In some examples, insulative cover 76 may have a thickness of about 300 micrometers to about 600 micrometers. Housing 15B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
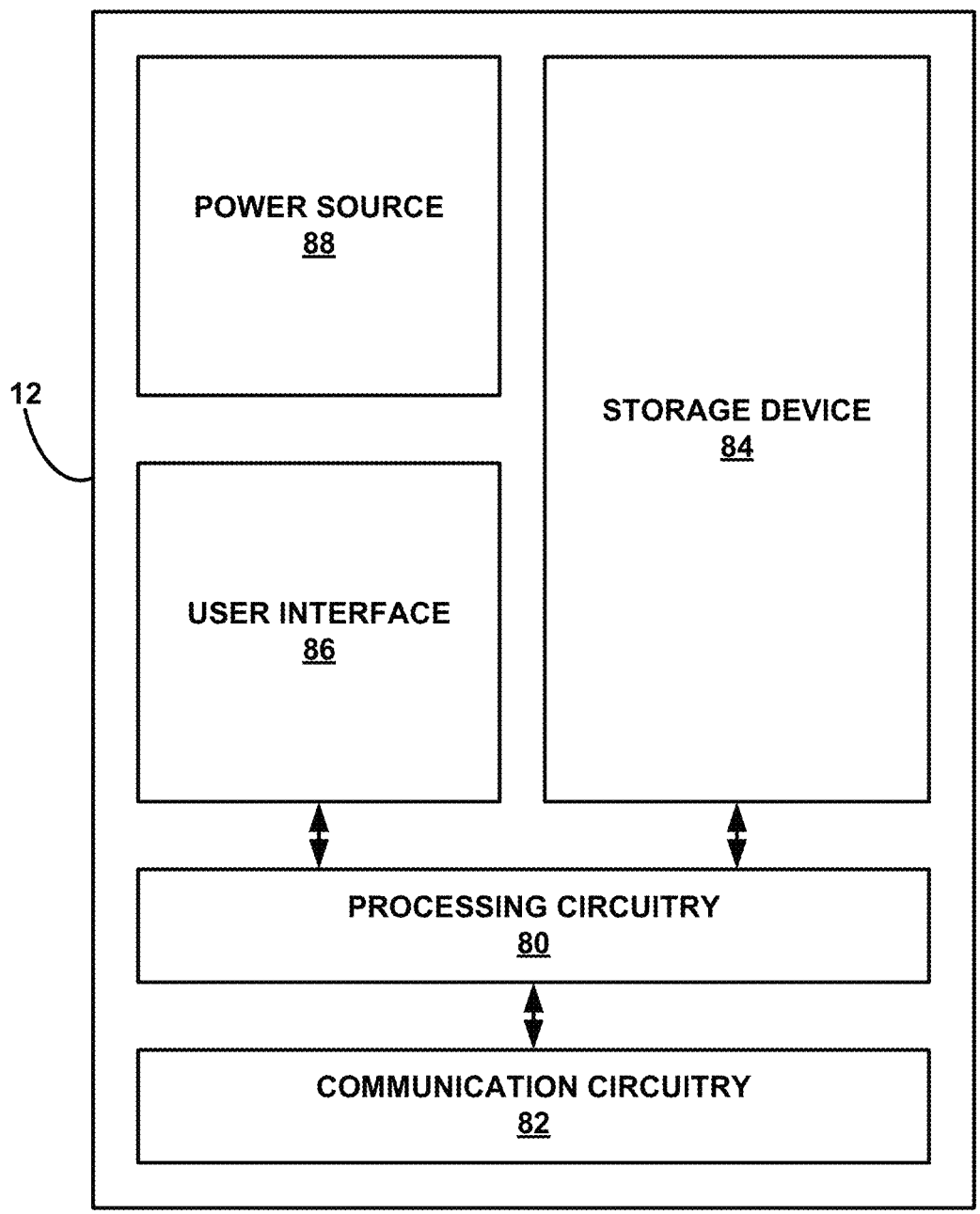
FIG. 5 is a block diagram illustrating an example configuration of components of the external device of FIG. 1, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, storage device 84, user interface 86, and power source 88.

Processing circuitry 80 may include fixed function circuitry and/or programmable processing circuitry. Processing circuitry 80 may include, for example, microprocessors, DSPs, ASICs, FPGAs, equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to external device 12. In some examples, processing circuitry 80 may represent at least a portion of processing circuitry 14 of FIG. 1, but this is not required. In some examples, processing circuitry 80 may be separate from processing circuitry 14 of FIG. 1.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

In some examples, storage device 84 includes computer-readable instructions that, when executed by processing circuitry 80, cause external device 12 and processing circuitry 80 to perform various functions attributed to IMD 10 and processing circuitry 80 herein. Storage device 84 may include one or both of a short-term memory or a long-term memory. The memory may include, for example, RAM, DRAM, SRAM, magnetic discs, optical discs, flash memories, or forms of EPROM or EEPROM. In some examples, the memory is used to store program instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data corresponding to one or both of a cardiac EGM signal and an accelerometer signal) to external device 12. In turn, external device 12 may receive the collected data from IMD 10 and store the collected data in storage device 84.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination, impedance signals, motion signals, cough counts, accelerometer signals including detected coughs, an impending symptom warning, or any combination thereof). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
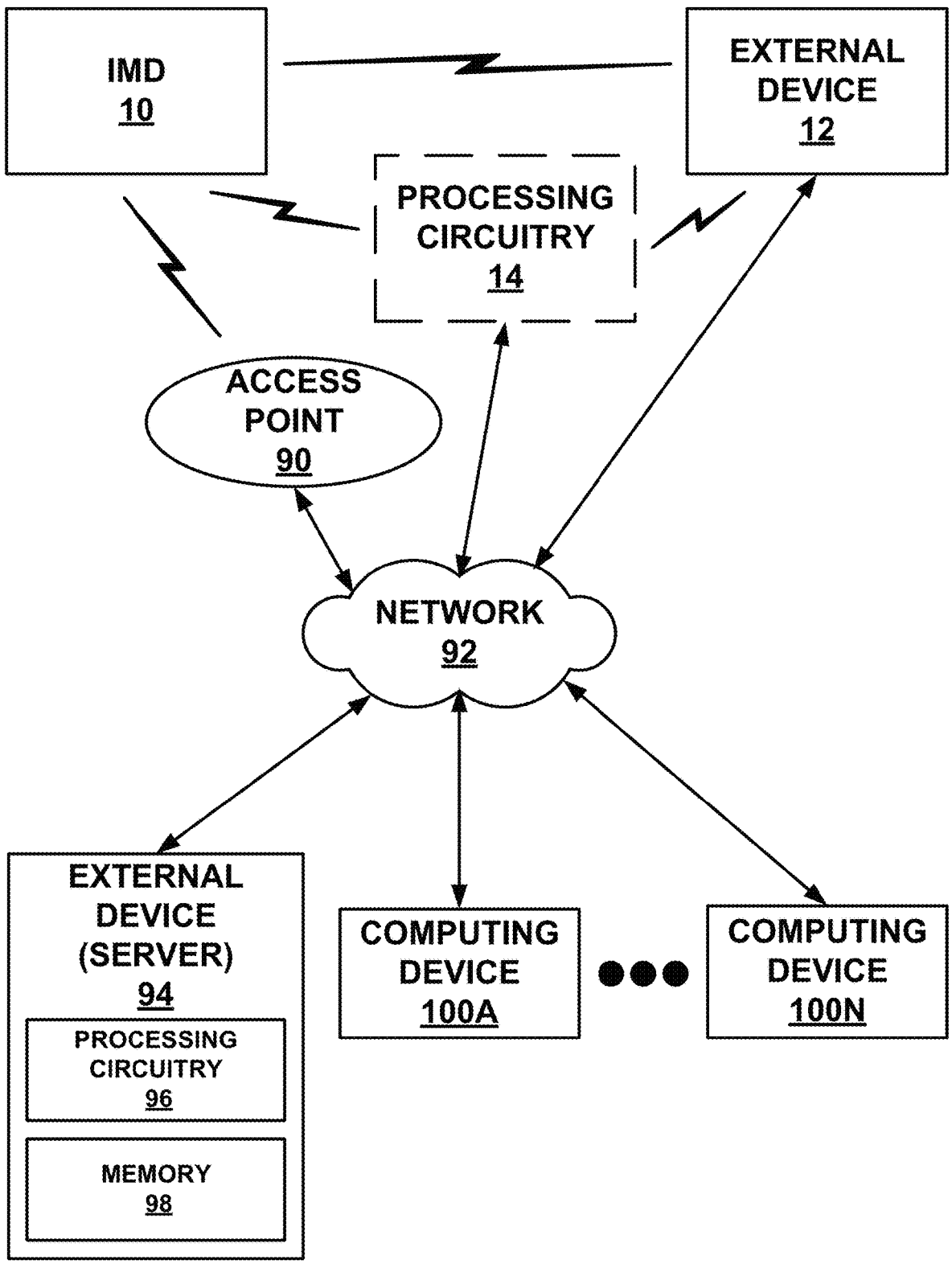
FIG. 6 is a block diagram illustrating an example system that includes an access point, a network, external computing devices, such as a server, and one or more other computing devices, which may be coupled to the IMD, the external device, and the processing circuitry of FIG. 1 via a network, in accordance with one or more techniques described herein.

FIG. 6 is a block diagram illustrating an example system that includes an access point 90, a network 92, external computing devices, such as a server 94, and one or more other computing devices 100A-100N, which may be coupled to IMD 10, external device 12, and processing circuitry 14 via network 92, in accordance with one or more techniques described herein. In this example, IMD 10 may use communication circuitry 54 to communicate with external device 12 via a first wireless connection, and to communication with an access point 90 via a second wireless connection. In the example of FIG. 6, access point 90, external device 12, server 94, and computing devices 100A-100N are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as any one or combination of an accelerometer signal, and a cough count to external device 12. In addition, access point 90 may interrogate IMD 10, such as periodically or in response to a command from the patient or network 92, in order to retrieve parameter values determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 6 may be implemented with general network technology and functionality, which may be similar to that provided by the Medtronic CareLink® Network developed by Medtronic plc, of Dublin, Ireland.

Server 94 may include processing circuitry 96. Processing circuitry 96 may include fixed function circuitry and/or programmable processing circuitry. Processing circuitry 96 may include any one or more of a microprocessor, a controller, a DSP, an ASIC, an FPGA, or equivalent discrete or analog logic circuitry. In some examples, processing circuitry 96 may include multiple components, such as any combination of one or more microprocessors, one or more controllers, one or more DSPs, one or more ASICs, or one or more FPGAs, as well as other discrete or integrated logic circuitry. The functions attributed to processing circuitry 96 herein may be embodied as software, firmware, hardware or any combination thereof. In some examples, processing circuitry 96 may perform one or more techniques described herein based on one or more sets of accelerometer data received from IMD 10, or may otherwise represent at least a portion of processing circuitry 14 of FIG. 1.

Server 94 may include memory 98. Memory 98 includes computer-readable instructions that, when executed by processing circuitry 96, cause IMD 10 and processing circuitry 96 to perform various functions attributed to IMD 10 and processing circuitry 96 herein. Memory 98 may include any volatile, non-volatile, magnetic, optical, or electrical media, such as RAM, ROM, NVRAM, EEPROM, flash memory, or any other digital media.

In some examples, one or more of computing devices 100A-100N (e.g., device 100A) may be a tablet or other smart device located with a clinician or physician, by which the clinician may program, receive alerts from, and/or interrogate IMD 10. For example, the clinician may access data corresponding to any one or more of an accelerometer signal, and a cough count collected by IMD 10 through device 100A, such as when patient 4 is in between clinician visits, to check on a status of a medical condition. In some examples, the clinician may enter instructions for a medical intervention for patient 4 into an app in device 100A, such as based on a status of a patient condition determined by IMD 10, external device 12, processing circuitry 14, or any combination thereof, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a status of a medical condition of patient 4 determined by IMD 10, external device 12, processing circuitry 14, or any combination thereof, which may enable patient 4 proactively to seek medical attention prior to receiving instructions for a medical intervention. In this manner, patient 4 may be empowered to take action, as needed, to address his or her medical status, which may help improve clinical outcomes for patient 4.

Figure 7:
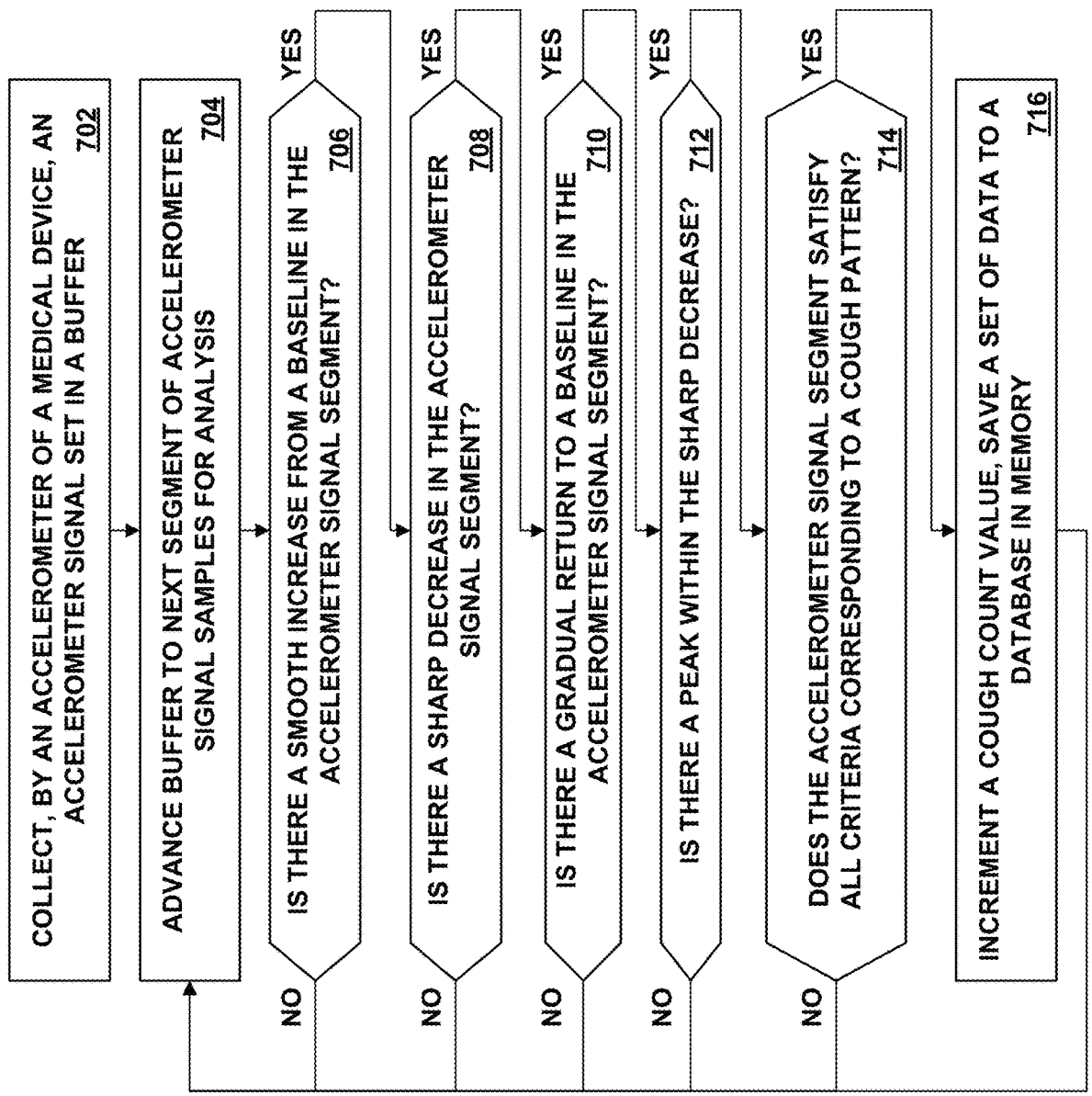
FIG. 7 is a flow diagram illustrating an example operation for identifying a cough event from an accelerometer signal, in accordance with one or more techniques of this disclosure.

FIG. 7 is a flow diagram illustrating an example operation for identifying a cough event from an accelerometer signal, in accordance with one or more techniques of this disclosure.

An accelerometer signal segment recorded by IMD 10 may have one or more features indicative of a cough, e.g., hard cough (or coughs). An algorithm executed on processing circuitry 14 may determine that a cough event occurs when all of a number of features are present in the accelerometer signal. In order to conserve computational power, especially for internal devices with a limited power source, processing circuitry 14 may check for features step-by-step, and upon failing to identify a feature that must be present in order for processing circuitry 14 to determine that a cough event has occurred, terminate further analysis of that particular accelerometer signal segment. Processing circuitry 14 may also terminate further analysis of a particular accelerometer signal segment if one of a plurality of steps executed in order to identify features of a cough event fails.

As illustrated by the example of FIG. 7, processing circuitry 14 may collect an accelerometer signal set in a buffer (702). The accelerometer signal may come from a frontal accelerometer integrated with IMD 10. The buffer may include a number of signal samples sufficient to detect all the features required to identify a cough.

An algorithm executed on processing circuitry 14 may analyze the next available segment of accelerometer signal samples in the buffer (704). For every iteration of the algorithm, it may advance the buffer to a next segment of accelerometer signal samples. The next segment of accelerometer signal samples may be offset from the prior segment by one or more samples, such that each next segment consists of one or more signal samples collected in a period of time after the one or more signal samples from the prior segment. In order to analyze the next segment of accelerometer signals, the algorithm may check the signal segment for a number of features. The algorithm may check for features in any order, and may move on to analyzing another signal segment if unable to identify a feature in the segment currently being analyzed. In order to identify these features, processing circuitry 14 may go through a number of other calculation and identification steps which may be performed in any order. The failure to calculate or identify in these other steps may also result in the algorithm moving on to analyzing another signal segment.

Processing circuitry 14 may identify a smooth increase in the accelerometer signal from a baseline (706). Although in FIG. 7 this feature is checked for first, the algorithm may check for other features first, and may not check for this feature at all if other features cannot be identified. In order to identify the smooth increase in the accelerometer signal from the baseline, processing circuitry 14 may perform one or more steps. Processing circuitry 14 may calculate the amplitude difference between each sample and one or more later samples in the sample segment being analyzed. For example, processing circuitry 14 may calculate the difference between each sample and the $5^{th}$ following sample, as well as each sample and the $10^{th}$ following sample. If the amplitude differences exceed certain values, processing circuitry 14 may determine that the segment of the accelerometer signal containing those samples is indicative of one or more patient upper body movements. The segment indicative of one or more patient upper body movements may include other samples before the samples for which amplitude differences were calculated, and other samples afterwards. If processing circuitry 14 does not identify a sample with amplitude differences between it and later samples exceeding threshold values, processing circuitry 14 may stop analyzing the accelerometer signal segment and move on to another accelerometer signal segment.

In order to identify the smooth increase in the accelerometer signal from the baseline, processing circuitry 14 may perform further calculations on the sample with amplitude differences between it and later samples exceeding threshold values (sample one). Processing circuitry 14 may define a first sample window in the long-term average signal a number of samples before and a number of samples after sample one. For example, processing circuitry 14 may define a first sample window spanning 20 samples before sample one and 10 samples after sample one. Within the first sample window, processing circuitry 14 may calculate the amplitude difference between each successive sample. The first negative difference calculated in the first sample window is determined to be a dropoff point in the long-term average signal and the accelerometer signal segment. Processing circuitry 14 may define a second sample window in the accelerometer signal segment including a number of samples before the dropoff point. For example, processing circuitry 14 may define the second sample window from 150 samples before the dropoff point to 50 samples before the dropoff point. Within the second sample window, processing circuitry 14 may identify a maximum and minimum amplitude value, and calculate the difference therebetween. If the difference between the maximum and minimum amplitude values in the second sample window exceeds a threshold value, processing circuitry 14 may determine that the increase in the accelerometer signal is not smooth, stop analyzing the accelerometer signal segment, and move on to another accelerometer signal segment. For example, if processing circuitry 14 calculates the difference between the maximum and minimum amplitude values in the second sample window to exceed 0.25, then processing circuitry 14 may determine that the increase in the accelerometer signal is not smooth. If processing circuitry 14 determines that the difference between the maximum and minimum amplitude values in the second sample window does not exceed a threshold value, processing circuitry 14 may determine that there is a smooth increase in the accelerometer signal segment from the baseline.

Processing circuitry 14 may identify a sharp decrease in the accelerometer signal segment (708). Although in FIG. 7 this feature is checked for second, the algorithm may check for other features second, and may not check for this feature at all if other features cannot be identified. In order to identify the sharp decrease in the accelerometer signal, processing circuitry 14 may define a valley point in the long-term average signal. Processing circuitry 14 may define a third sample window consisting of a predetermined number of samples immediately following the dropoff point. For example processing circuitry 14 may define the third sample window as the 350 samples immediately following the dropoff point. Processing circuitry 14 may then calculate a second first-difference signal from the third sample window. For each point in the second first-difference signal, processing circuitry 14 may define an earlier window and a later window, consisting of a predetermined number of samples before and after the point respectively. For example, processing circuitry 14 may define an earlier window of 15 samples before each point and a later window of 15 samples after each point in the second first-difference signal. Processing circuitry 14 may analyze each earlier and later window to determine if the values in those windows are positive or negative, as the values of the second first-difference signal will be representative of a slope of the long-term average signal. If a predetermined majority of samples in the earlier window are negative, and a predetermined majority of samples in the later window are positive, processing circuitry 14 may define the sample point around which those windows sit as the valley point. For example, if 14 out of 15 sample points in the earlier window are negative, and 14 out of 15 sample points in the later window are positive, processing circuitry 14 may define the point around which those two windows sit as the valley point. If processing circuitry 14 does not identify any point in the second first difference signal where the predetermined number of earlier samples are negative and the predetermined number of later samples are positive, processing circuitry 14 may stop analyzing the accelerometer signal segment, and move on to another accelerometer signal segment.

After identifying a valley point, processing circuitry 14 may determine if the amplitude difference between the dropoff point and the valley point in the long-term average signal is within a first range. For example, processing circuitry 14 may determine if the amplitude difference between the dropoff point and the valley point is greater than 0.2 and less than 0.6. If the amplitude difference between the dropoff point and the valley point is within the first range, processing circuitry 14 may identify the sample window between the dropoff point and the valley point as the sharp decrease in the accelerometer signal.

Processing circuitry 14 may identify a gradual return to a baseline in the accelerometer signal (710). Although in FIG. 7 this feature is checked for third, the algorithm may check for other features third, and may not check for this feature at all if other features cannot be identified. In order to identify the gradual return of the accelerometer signal to the baseline, processing circuitry 14 may define a stabilization point. The stabilization point may be identified by first defining a fourth sample window within the second first-difference signal. The fourth sample window may consist of a number of samples between the valley point and the end of the second first-difference signal. For example, processing circuitry 14 may define the fourth sample window as starting 15 samples after the valley point and ending at the end of the second first-difference window. Within the fourth sample window, processing circuitry 14 identifies the first negative value point. Then a fifth sample window may be defined a predetermined number of samples after the first negative value point. For example, the fifth sample window may be defined as 25 samples after the first negative value point. Within the fifth sample window, processing circuitry 14 may determine how many point values are negative and how many are positive. If there are too many positive values and/or too few negative values, processing circuitry 14 may determine that the first negative value point does not correspond to a stabilization point, and perform the operation described in this paragraph on the second negative value point in the fourth sample window. For example, if there are 1 or fewer negative point values in the fifth sample window, and/or 4 or more positive point values in the fifth sample window, processing circuitry 14 may determine that the first negative value does not correspond to a stabilization point, and perform the operation described in this paragraph on the second negative value point in the fourth sample window. If there are few enough positive values and enough negative values in the fifth sample window following a negative value point, processing circuitry 14 may determine that the negative value point is satisfactory.

If processing circuitry 14 does not identify any negative value points in the fourth sample window, processing circuitry may determine if there are a predetermined number of consecutive zero values in the fourth sample window. If there are a predetermined number of consecutive zero values in the fourth sample window, processing circuitry 14 may define the first of the consecutive zero values as the stabilization point. For example, if processing circuitry 14 determines there are 20 consecutive zero values in the fourth sample window, processing circuitry 14 may define the first of the 20 consecutive zero values as the stabilization point. If there are no satisfactory negative value points, and no predetermined number of consecutive zero values in the fourth sample window, processing circuitry 14 may stop analyzing the accelerometer signal segment and move on to another accelerometer signal segment.

If processing circuitry 14 does identify a satisfactory negative value point, processing circuitry may define the stabilization point as the satisfactory negative value point, but first, processing circuitry 14 performs another check. Processing circuitry 14 may define a sixth sample window in the second first-difference signal. The sixth sample window be defined from a range of samples between the valley point and the satisfactory negative value point. For example, processing circuitry 14 may define the sixth sample window to be the range of samples between the valley point and 25 samples before the satisfactory negative value point. Within the sixth sample window, processing circuitry 14 determines if there are a predetermined number of consecutive zero values. If the predetermined number of consecutive zero values is present in the sixth sample window, processing circuitry 14 may define the first zero value point as the stabilization point. If the predetermined number of consecutive zero values is not present in the sixth sample window, processing circuitry 14 may define the satisfactory negative value point as the stabilization point. For example, processing circuitry 14 may check the sixth sample window for 25 consecutive zero values. If there are 25 consecutive zero values, processing circuitry 14 may define the first zero value as the stabilization point. If there are not 25 consecutive zero values, processing circuitry 14 may define the satisfactory negative value point as the stabilization point.

Processing circuitry 14 may determine if there is a gradual return to a baseline in the accelerometer signal with reference to the stabilization point. Processing circuitry 14 may determine if the amplitude difference between the stabilization point and the valley point is smaller than a threshold value, and if a ratio of the number of samples between the stabilization point and valley point to the sampling rate is within a second range. For example, processing circuitry 14 may determine if the amplitude difference between the stabilization point and the valley point is less than 0.4, and if the number of samples between the stabilization point and valley point is between 80 and 220 when the sampling rate is 100 Hz. If the amplitude difference between the stabilization point and the valley point is smaller than a threshold value, and if a ratio of the number of samples between the stabilization point and valley point to the sampling rate is within a second range, processing circuitry 14 may identify the sample window between the valley point and the stabilization point as a slow return to a baseline in the accelerometer signal.

Processing circuitry 14 may identify a peak within the sharp decrease in the accelerometer signal (712). Although in FIG. 7 this feature is checked for fourth, the algorithm may check for other features fourth, and may not check for this feature at all if other features cannot be identified. The algorithm may check for this feature any time after identifying a sharp decrease in the accelerometer signal. In order to identify the peak within the sharp decrease in the accelerometer signal, processing circuitry 14 may define a seventh sample window in the accelerometer signal. The seventh sample window may be defined as the samples between the dropoff point and the valley point in the accelerometer signal. Processing circuitry 14 may then create a difference signal from the seventh sample window by computing the amplitude difference with every fourth sample in the seventh sample window. If the difference signal contains a positive threshold crossing and a negative threshold crossing, processing circuitry 14 may determine that there is a peak within the seventh sample window, and thus within the sharp decline. For example, if the difference signal has at least one positive threshold crossing with a threshold of 0.08 and at least one negative threshold crossing with a threshold of −0.08, then processing circuitry 14 may determine that there is a peak within the seventh sample window. If processing circuitry 14 does not detect sufficient positive and negative threshold crossings in the difference signal of the seventh sample window, then processing circuitry 14 may stop analyzing the accelerometer signal segment and move on to another accelerometer signal segment.

Processing circuitry 14 may check to see if the accelerometer signal segment has features that satisfy all the criteria corresponding to a cough (714). If one or more features were not identified, or one or more criteria not met, processing circuitry 14 may stop analyzing the accelerometer signal segment and move on to another accelerometer signal segment (704). If processing circuitry 14 did identify all relevant features satisfying all criteria, processing circuitry 14 may increment a cough count value, save a set of data to a database in memory (716), and notify a physician of the data set.

Processing circuitry 14 may also check for features indicative of bad data. For example, processing circuitry 14 may check for excessive noise in the accelerometer signal segment. If excessive noise is detected, the algorithm may determine that the accelerometer signal segment is indicative of a bad data rather than a cough. The algorithm may check for excessive noise at any time, and may not check for excessive noise if other features indicative of a cough, cannot be identified. Processing circuitry 14 may determine excessive noise is present in the accelerometer signal in a number of ways. In some examples, processing circuitry 14 may determine that an accelerometer signal segment is too noisy if a number of accelerometer sample values exceed a first threshold, wherein the sample values fluctuate in value a number of times above a second threshold, and the excessive number of excessively fluctuating accelerometer sample values occur in the accelerometer signal during an amount of time less than a third threshold amount.

Figure 8:
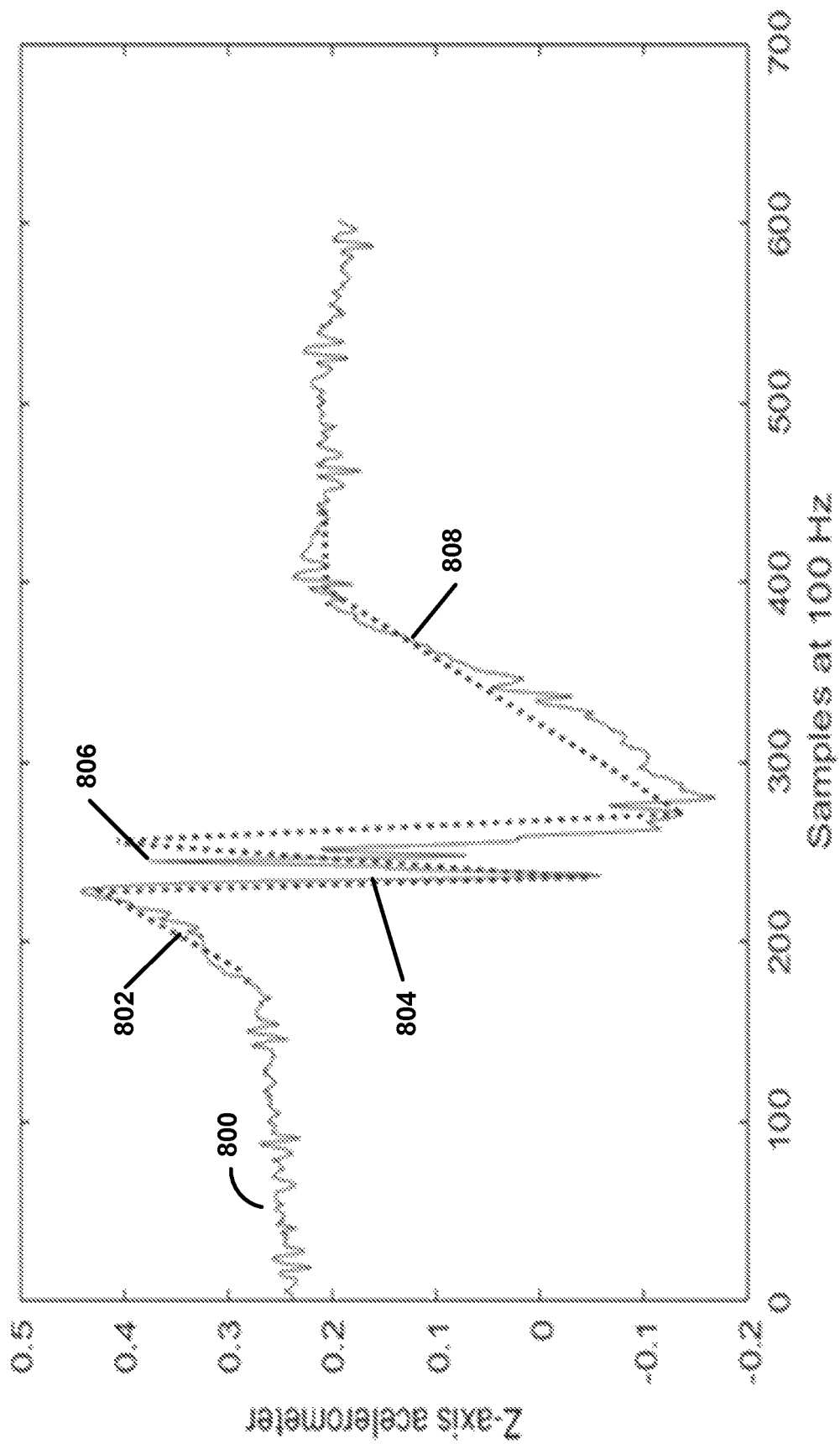
FIG. 8 is a graph illustrating an example accelerometer signal during a cough, highlighting features indicative of a cough, in accordance with one or more techniques of this disclosure.

FIG. 8 is a graph illustrating an example accelerometer signal during a cough, highlighting features indicative of a cough, in accordance with one or more techniques of this disclosure.

Accelerometer signal 800 may contain features indicative of a cough e.g., hard cough (or coughs), such as a smooth increase 802 in the accelerometer signal from the baseline, a sharp decrease 804 in the accelerometer signal, a peak 806 within the sharp decrease, and a gradual return 808 of the accelerometer signal to the baseline. The algorithm may check for features in any order, and may move on to analyzing another signal segment if unable to identify a feature in the segment currently being analyzed. The process for identifying these features is described in more detail above with reference to FIG. 7.

Figure 9:
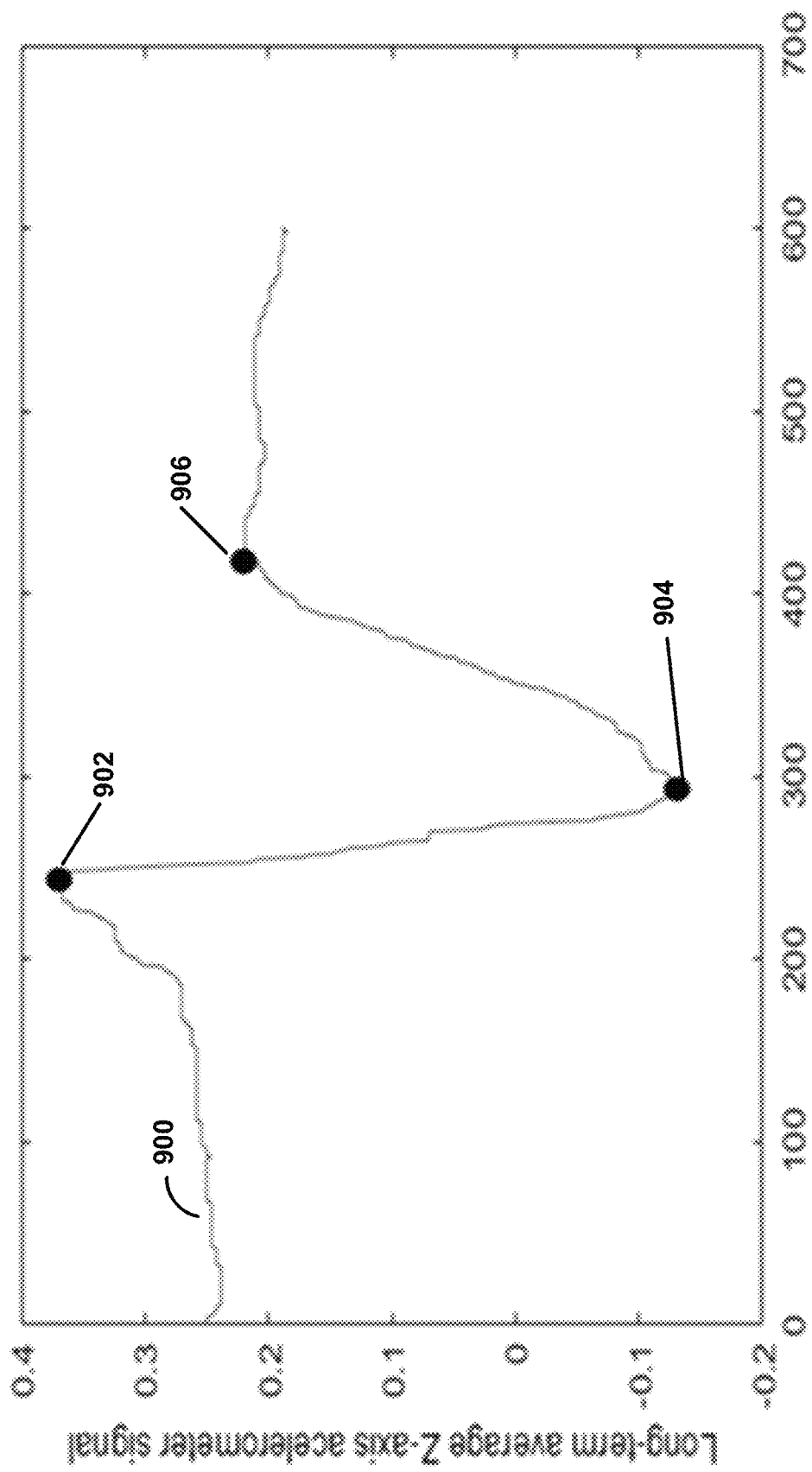
FIG. 9 is a graph illustrating an example long-term average signal of the accelerometer signal of FIG. 8, highlighting features indicative of a cough, in accordance with one or more techniques of this disclosure.

FIG. 9 is a graph illustrating an example long-term average signal of the accelerometer signal of FIG. 8, highlighting features indicative of a cough, in accordance with one or more techniques of this disclosure.

In some examples, it may be easier for processing circuitry 14 to detect features of a cough event in the long-term average signal 900. Processing circuitry 14 may define points within the long-term average signal, including a dropoff point 902, a valley point 904, and a stabilization point 906.

Processing circuitry 14 may determine if the features identified in the long-term average signal satisfy criteria corresponding to a cough. Processing circuitry 14 may determine if the amplitude difference between the dropoff point and the valley point is within a first range, if the amplitude difference between the stabilization point and the valley point is smaller than a threshold value, and if a ratio of the number of samples between the stabilization point and valley point to the sampling rate is within a second range. For example, processing circuitry 14 may determine if the amplitude difference between the dropoff point and the valley point is greater than 0.2 and less than 0.6, if the amplitude difference between the stabilization point and the valley point is less than 0.4, and if the number of samples between the stabilization point and valley point is between 80 and 220 when the sampling rate is 100 Hz. The process for identifying these features and checking for these criteria is described in more detail above with reference to FIG. 7.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device system comprising:
 a medical device comprising:
  an accelerometer configured to continuously collect an accelerometer signal as digital signal data, wherein the accelerometer signal is indicative of one or more patient movements that occur during a cough; and
 processing circuitry configured to:
  determine, based on a frontal component of the signal data, whether the accelerometer signal satisfies each criterion of a set of criteria corresponding to a cough pattern, wherein the set of criteria comprises:
   a smooth increase from a baseline;
   a sharp decrease after the smooth increase;
   a peak within the sharp decrease wherein the peak occurs in the accelerometer signal at a sample between a dropoff point and a valley point of a long-term average signal determined from the accelerometer signal; and
   a gradual return to the baseline after the sharp decrease; and
  identify a cough based on the determination that the accelerometer signal satisfies all criterion of the set of criteria.

2. The medical device system of claim 1, wherein the processing circuitry is further configured to increment a cough count value based on the identification of the cough.

3. The medical device system of claim 1, wherein the processing circuitry is further configured to:
 Save, to a database in memory, a set of data including the signal data; and
 notify a physician of the data set.

4. The medical device system of claim 1, wherein to determine whether the accelerometer signal satisfies the set of criteria corresponding to a cough pattern, the processing circuitry is further configured to:
 execute an algorithm in a series of steps determining whether each criterion of the set of criteria is satisfied individually; and
 terminate the algorithm without proceeding to the later steps responsive to one of the criteria not being satisfied.

5. The medical device system of claim 4, wherein to perform the series of steps, the processing circuitry is further configured to:
 determine the long-term average signal from the accelerometer signal;
 identify the dropoff point in the long-term average signal;
 identify the valley point in the long-term average signal; and
 identify a stabilization point in the long-term average signal.

6. The medical device system of claim 5, wherein to perform the series of steps, the processing circuitry is further configured to:
 determine whether an amplitude difference between the dropoff point and the valley point is greater than a threshold value.

7. The medical device system of claim 5, wherein to perform the series of steps, the processing circuitry is further configured to:
 determine whether an amplitude difference between the stabilization point and the valley point is less than a threshold value.

8. The medical device system of claim 5, wherein to perform the series of steps, the processing circuitry is further configured to:
 determine whether a ratio of a number of samples between the stabilization point and valley point to a sampling rate is both above a first threshold value and below a second threshold value.

9. The medical device system of claim 5, wherein to perform the series of steps, the processing circuitry is further configured to:
 determine if noisy fluctuations exist in the accelerometer signal preceding the dropoff point in the long-term average signal.

10. The medical device system of claim 5, wherein to perform the series of steps, the processing circuitry is further configured to:
 determine if the peak point exists between the dropoff point and the valley point wherein to determine that the peak point exists, the processing circuitry is configured to determine that a difference signal between the dropoff point and the valley point contains a first value above a first threshold value and a second value below a second threshold value.

11. A method of operating a medical device system comprising a medical device, the method comprising:
 collecting, using an accelerometer of the medical device, an accelerometer signal as digital signal data, wherein the accelerometer signal is indicative of one or more patient movements that occur during a cough;
 determining, by processing circuitry of the medical device system and based on a frontal component of the signal data, whether the accelerometer signal satisfies each criterion of a set of criteria corresponding to a cough pattern, wherein the set of criteria comprises:
  a smooth increase from a baseline;
  a sharp decrease after the smooth increase;
  a peak within the sharp decrease wherein the peak occurs in the accelerometer signal at a sample between a dropoff point and a valley point of a long-term average signal determined from the accelerometer signal; and
  a gradual return to the baseline after the sharp decrease; and
 identifying, by the processing circuitry, a cough based on determining that the accelerometer signal satisfies all criterion of the set of criteria.

12. The method of claim 11, wherein the method further comprises incrementing, by the processing circuitry, a cough count value in response to identifying the cough.

13. The method of claim 11, wherein the method further comprises:
 saving, by the processing circuitry, to a database in memory, a set of data including the signal data; and
 notifying, by the processing circuitry, a physician of the data set.

14. The method of claim 11, wherein determining whether the accelerometer signal satisfies the set of criteria corresponding to a cough pattern further comprises:
 executing, by the processing circuitry, an algorithm in a series of steps determining whether each criterion of the set of criteria is satisfied individually; and
 terminating, by the processing circuitry, the algorithm without proceeding to the later steps responsive to one of the criteria not being satisfied.

15. The method of claim 14, wherein the series of steps comprises:
 determining, by the processing circuitry, the long-term average signal from the accelerometer signal;
 identifying, by the processing circuitry, the dropoff point in the long-term average signal;
 identifying, by the processing circuitry, the valley point in the long-term average signal; and
 identifying, by the processing circuitry, a stabilization point in the long-term average signal.

16. The method of claim 15, wherein the series of steps further comprises:
 determining, by the processing circuitry, whether an amplitude difference between the dropoff point and the valley point is greater than a threshold value.

17. The method of claim 15, wherein the series of steps further comprises determining, by the processing circuitry, whether an amplitude difference between the stabilization point and the valley point is less than a threshold value.

18. The method of claim 15, wherein the series of steps further comprises determining, by the processing circuitry, whether a ratio of a number of samples between the stabilization point and valley point to a sampling rate is both above a first threshold value and below a second threshold value.

19. The method of claim 15, wherein the series of steps further comprises:
 determining, by the processing circuitry, if noisy fluctuations exist in the accelerometer signal preceding the dropoff point in the long-term average signal; and
 determining, by the processing circuitry, if the peak point exists between the dropoff point and the valley point wherein to determine that the peak point exists, the processing circuitry is configured to determine that a difference signal between the dropoff point and the valley point contains a first value above a first threshold value and a second value below a second threshold value.

20. A non-transitory computer-readable medium comprising instructions for causing processing circuitry of a medical device system to:
 determine whether a frontal component of an accelerometer signal satisfies each criterion of a set of criteria corresponding to a cough pattern, wherein the set of criteria comprises:
  a smooth increase from a baseline;
  a sharp decrease after the smooth increase;
  a peak within the sharp decrease wherein the peak occurs in the accelerometer signal at a sample between a dropoff point and a valley point of a long-term average signal determined from the accelerometer signal; and
  a gradual return to the baseline after the sharp decrease,
 wherein the accelerometer signal is collected by an accelerometer of a medical device as digital signal data, and is indicative of one or more patient movements that occur during a cough; and
 identify a cough based on the determination that the accelerometer signal satisfies all criterion of the set of criteria.

* * * * *